US011250958B2

(12) United States Patent
Asthana et al.

(10) Patent No.: US 11,250,958 B2
(45) Date of Patent: Feb. 15, 2022

(54) SYSTEMS AND TECHNIQUES FOR RECOMMENDING PERSONALIZED HEALTH CARE BASED ON DEMOGRAPHICS

(71) Applicant: International Business Machines Corporation, Armonk, NY (US)

(72) Inventors: Shubhi Asthana, Santa Clara, CA (US); Hovey R. Strong, Jr., San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 1247 days.

(21) Appl. No.: 15/331,630

(22) Filed: Oct. 21, 2016

(65) Prior Publication Data

US 2018/0113982 A1    Apr. 26, 2018

(51) Int. Cl.
*G16H 70/60* (2018.01)
*G06N 5/04* (2006.01)
(Continued)

(52) U.S. Cl.
CPC ......... *G16H 70/60* (2018.01); *G06F 16/2246* (2019.01); *G06F 16/288* (2019.01);
(Continued)

(58) Field of Classification Search
CPC .................................................. G06Q 20/387
(Continued)

(56) References Cited

U.S. PATENT DOCUMENTS 7,103,534 B2 * 9/2006 Goodman ............. G06F 40/274
704/9
7,542,947 B2   6/2009 Guyon et al.
(Continued)

OTHER PUBLICATIONS

"A New Decision Tree Method for Data Mining in Medecine," Kasra Madadipouya, Advanced Computational Intelligence: An International Journal (ACII), vol. 2, No. 3, Jul. 2015 (Year: 2015).*
(Continued)

*Primary Examiner* — Joshua B Blanchette
(74) *Attorney, Agent, or Firm* — Zilka-Kotab, P.C.

(57) ABSTRACT

Computer program products are configured to perform methods for determining likely health conditions based on demographic information and/or determining appropriate wearable technology and services to monitor a patient's health. In one embodiment, a computer program product is configured to perform a method including receiving historical demographic data comprising a plurality of attributes; associating the historical demographic data with labels corresponding to known causes of particular health conditions; building a decision tree model using the historical demographic data and the associated label(s); generating a vector $Y_k$ using the model, $Y_k$ representing probable causes of a plurality of health conditions; and determining likely health conditions for a patient based on comparing the vector $Y_k$ to a second vector $Z_k$, $Z_k$ representing probable causes of health conditions determined based on a health care record for the patient. Appropriate wearables for tracking the health of the patient may be determined using textual analysis.

19 Claims, 5 Drawing Sheets

(51) Int. Cl.
*G16H 50/20* (2018.01)
*G16H 10/60* (2018.01)
*G06F 16/28* (2019.01)
*G06N 5/02* (2006.01)
*G16H 50/70* (2018.01)
*G06F 16/22* (2019.01)

(52) U.S. Cl.
CPC ............ *G06N 5/025* (2013.01); *G06N 5/045* (2013.01); *G16H 10/60* (2018.01); *G16H 50/20* (2018.01); *G16H 50/70* (2018.01)

(58) Field of Classification Search
USPC ........................................................ 705/2, 3
See application file for complete search history.

(56) References Cited

U.S. PATENT DOCUMENTS

| | | | |
|---|---|---|---|
| 8,145,590 | B2 | 3/2012 | Brockway et al. |
| 8,684,922 | B2 | 4/2014 | Tran |
| 8,714,983 | B2 | 5/2014 | Kil |
| 8,930,212 | B2 | 1/2015 | Oakley et al. |
| 9,107,586 | B2 | 8/2015 | Tran |
| 9,215,980 | B2 | 12/2015 | Tran et al. |
| 9,262,772 | B2 | 2/2016 | Stivoric et al. |
| 9,307,944 | B2 | 4/2016 | Colman et al. |
| 2003/0050915 | A1* | 3/2003 | Allemang ............ G06F 16/9024 |
| 2007/0094048 | A1* | 4/2007 | Grichnik ................ G16H 50/30 705/2 |
| 2011/0166879 | A1* | 7/2011 | Lee ........................ G16H 50/70 705/2 |
| 2012/0165617 | A1 | 6/2012 | Vesto et al. |
| 2015/0269825 | A1 | 9/2015 | Tran |
| 2015/0332014 | A1* | 11/2015 | Konno ................... G16H 50/50 705/2 |

OTHER PUBLICATIONS

"Wearable Sensors: Opportunities and Challenges for Low-Cost Health Care," Richard R. Fletcher et al., 32nd Annual International Conference of the IEEE EMBS Buenos Aires, Argentina, Aug. 31-Sep. 4, 2010 (Year: 2010).*

"Scoring and Selecting Terms for Text Categorization" by Elena Montanes et al., IEEE Intelligent Systems ( vol. 20, Issue: 3, May-Jun. 2005) (Year: 2005).*

Ashby et al., "Evidence-Based Medicine as Bayesian Decision-Making," Statistics in Medicine, 2000, pp. 1-15.

Khalila et al., "Predicting Disease Risks From Highly Imbalanced Data Using Random Forest," BMC Medical Informatics and Decision Making, 2011, pp. 1-13.

Spiegelhalter et al., "Statistical and Knowledge-Based Approaches to Clinical Decision-Support Systems, with an Application in Gastroenterology," J. R. Statist. Soc. A, 1984, 147, pp. 35-77.

Jensen, "Introduction to Bayesian Networks," Advanced Hard Management, Sep. 2009, pp. 1-8.

GNS Healthcare, "MAX Architecture," Aug. 6, 2016, pp. 1-5, Retrieved From https://web.archive.org/web/20160806035715/http://www.gnshealthcare.com/technology-overview/technology/.

Janssens et al., "Genome-Based Prediction of Common Diseases: Advances and Prospects," Human Molecular Genetics, 2008, vol. 17, Review Issue 2, pp. 166-173.

Wray et al., "Prediction of Individual Genetic Risk to Disease From Genome-Wide Association Studies," Genome Research, 2007, pp. 1520-1528.

Krishnamurthy et al., "SystemT: A System for Declarative Information Extraction," SIGMOD Record, vol. 37, No. 4, Dec. 2008, pp. 7-13.

IBM BigInsights on Cloud, "Hadoop-As-A-Service, Big Data Analytics In The Cloud," Apr. 28, 2016, pp. 1, Retrieved From http://www-03.ibm.com/software/products/en/ibm-biginsights-on-cloud.

Mascarenhas, "Willis Towers Watson Develops New Technology To More Accurately Predict When You're Going To Die," International Business Times, Apr. 4, 2016, pp. 1-3, Retrieved From http://www.ibtimes.co.uk/willis-towers-watson-develops-new-technology-more-accurately-predict-when-youre-going-die-1553048.

Khalilia, "Predicting Disease Risks From Highly Imbalanced Data Using Random Forest," BMC Medical Informatics and Decision Making, Jul. 29, 2011, pp. 1-13, Retrieved From http://bmcmedinformdecismak.biomedcentral.com/articles/10.1186/1472-6947-11-51.

MAYO Clinic, "Heart Disease Risk Calculator," Jan. 30, 2014, pp. 1-4, Retrieved From http://www.mayoclinic.org/diseases-conditions/heart-disease/in-depth/heart-disease-risk/itt-20084942.

* cited by examiner

SYSTEMS AND TECHNIQUES FOR RECOMMENDING PERSONALIZED HEALTH CARE BASED ON DEMOGRAPHICS

BACKGROUND

The present invention relates to health care, and more specifically, this invention relates to recommending personalized health care based on patient demographics.

Health care is a vitally important aspect of the modern economy and requires using a complex set of information to accurately diagnose patients and recommend appropriate treatment. With the advance of electronic health care records, data-driven health care is an increasing area of interest to health care professionals, and may improve the quality and efficiency with which health care services are provided and patient treatment is accomplished.

In addition, the rising popularity of portable sensors and devices to monitor health conditions provides additional opportunities to observe health status progression with precise metrics. However, currently existing sensors and devices do not provide the ability to monitor all relevant health metrics, and the use of such sensors and devices does not occur to all health care professionals, ultimately leaving a gap between the information needed to improve health care and the ability to collect such information.

Accordingly, it would be advantageous to provide systems and techniques configured to facilitate patient treatment and health care monitoring with a data-driven approach using portable sensors and devices.

SUMMARY

In one embodiment, a computer program product for determining likely health conditions based on demographic information includes a computer readable storage medium having program instructions embodied therewith, where the computer readable storage medium is not a transitory signal per se. The program instructions are executable by a processor to cause the processor to perform a method including: receiving historical demographic data comprising a plurality of attributes; associating the historical demographic data with one or more labels each independently corresponding to a known cause of a particular health condition; building a decision tree model based at least in part on the historical demographic data and the one or more labels associated therewith; generating, based on the decision tree model, a vector $Y_k$ representing one or more most probable causes of one or more of a plurality of health conditions; and determining one or more most likely health conditions for a patient based on comparing the vector $Y_k$ to a second vector $Z_k$, the second vector representing one or more most probable causes of one or more of the plurality of health conditions determined based on a health care record for the patient.

In accordance with another embodiment, a computer program product for determining appropriate wearable technology and services to monitor a patient for a likely health condition includes a computer readable storage medium having program instructions embodied therewith, where the computer readable storage medium is not a transitory signal per se. The program instructions are executable by a processor to cause the processor to perform a method including: receiving textual data from one or more medical journals and one or more patient health records; identifying one or more concepts by applying one or more query rules to the textual data; generating an entity relationship graph based on the concepts; searching the entity relationship graph to determine one or more measurements associated with one or more most probable health conditions; and determining one or more wearable technologies associated with the one or more measurements.

In yet another embodiment, a method for determining likely health conditions based on demographic information includes: receiving historical demographic data comprising a plurality of attributes; associating the historical demographic data with one or more labels each independently corresponding to a known cause of a particular health condition; building a decision tree model based at least in part on the historical demographic data and the one or more labels associated therewith; generating, based on the decision tree model, a vector $Y_k$ representing one or more most probable causes of one or more of a plurality of health conditions; and determining one or more most likely health conditions for a patient based on comparing the vector $Y_k$ to a second vector $Z_k$, the second vector representing one or more most probable causes of one or more of the plurality of health conditions determined based on a health care record for the patient.

Other aspects and embodiments of the present invention will become apparent from the following detailed description, which, when taken in conjunction with the drawings, illustrate by way of example the principles of the invention.

DETAILED DESCRIPTION

Figure 1:
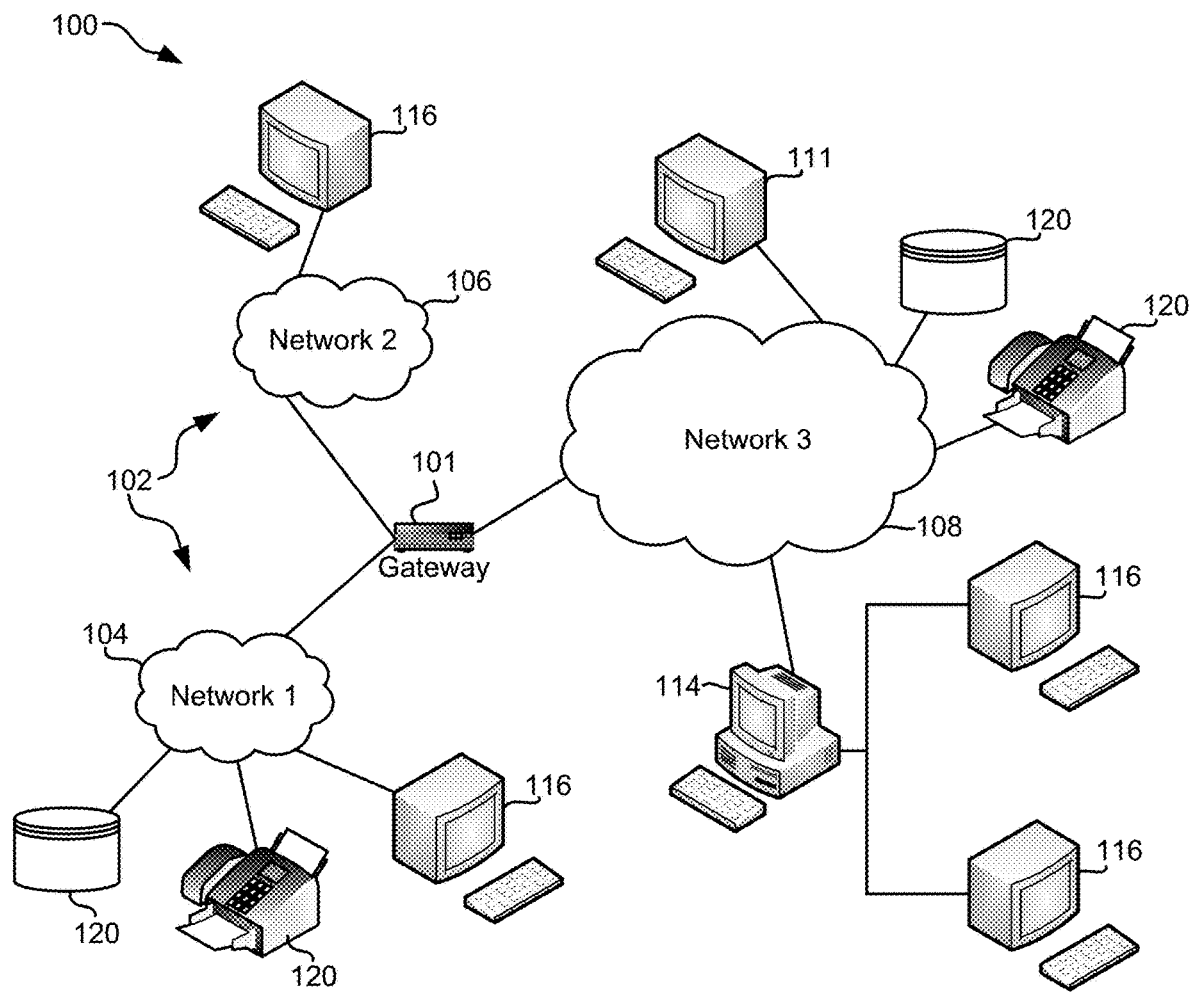
FIG. 1 illustrates a network architecture, in accordance with one embodiment.

The following description discloses several preferred embodiments of systems, methods and computer program products for adjusting aspects of a moving platform. Various embodiments provide a method to provide personalized health care to patients based on demographics.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified. It will be further understood that the terms "includes" and/or "comprising," when used in this specification, specify the presence of stated features, integers, steps, operations, elements, and/or components, but do not preclude the presence or addition of one or more other features, integers, steps, operations, elements, components, and/or groups thereof.

The term "independently" as recited herein and applied to members of a group, e.g. one or more labels each independently corresponding to a known cause of a particular health condition, is to be understood as meaning each member of the group individually satisfies the stated condition. In the context of the foregoing example, each label corresponds to a known cause of a particular health condition, but different labels may correspond to different health conditions, or the same health condition, in any possible combination or permutation that would be appreciated by a person having ordinary skill in the art upon reading the present disclosures.

The following description discloses several preferred embodiments of systems, methods and computer program products for providing personalized health care to patients based on demographics. More particularly, techniques for predicting likely health conditions for a patient based on demographics, as well as recommending suitable wearable technology to observe occurrence and/or progression of or toward particular health conditions are proposed.

In providing personalized health care to a particular patient population, it is advantageous to predict the major causes of health issues associated with particular patients based on a large demography dataset and personal health history. Given the historical data about demography and personal health, the presently disclosed inventive concepts involve identifying relationships between different demographic attributes and personal health history; predicting the major causes of health issues (e.g. risk factors) associated with health conditions likely to be experienced by the particular patient based on their demographics; and recommend personalized health care accordingly. The personalized health care may include treatment, preventative medicine, and/or observation of biological characteristics (e.g. pulse, blood pressure, cholesterol levels, breathing rate and/or volume, concentration of particular compounds in particular locations or media within the body such as specific oxygen in blood, gene expression levels in particular cell types or organs, etc. as would be understood by a person having ordinary skill in the art of diagnostic and/or predictive medicine, according to various embodiments) using suitable wearable technology.

Accordingly, the presently disclosed inventive concepts represent a technological improvement to the field of diagnostic and/or preventative medicine, in that likely health conditions that a particular patient may exhibit can be predicted with confidence based on demographics of the patient and a large volume of historical health data organized according to demographics. Furthermore, upon identifying likely health conditions for a particular patient, potential causes, risk factors, etc. corresponding to the likely health conditions may be determined, e.g. based on textual analysis of a vast volume of medical and/or academic publications and/or medical data, and appropriate monitoring, treatment, etc. may be recommended in a personalized manner to provide the best quality of care to the patient.

Notably, conventional diagnostic and preventative medicine techniques are incapable of providing the level of confidence in predicting likely health conditions and recommending appropriate monitoring or treatment, because it is practically impossible for health practitioners to parse the vast amount of data represented in the publications and/or medical data. Accordingly, physicians, nurses, and other health care professionals are not capable of reviewing all the pertinent information for each possible combination of demographics that may provide a useful prediction as to likely health conditions and appropriate monitoring for the patient. As a result, health care professionals typically limit diagnoses, prognoses, etc. based on the health care records for the individual patient, coupled with the professional's personal knowledge and experience. The presently disclosed inventive concepts represent an improvement over this conventional paradigm by expanding the data considered in predicting health conditions beyond a patient's individual records and a professional's personal knowledge and experience to include data corresponding to a large number of patients sharing the same set of demographics as the patient for which the health condition is to be predicted.

Moreover, with particular respect to monitoring, medical and academic literature relating to particular health conditions does not typically include information regarding appropriate wearable technology that may be utilized to monitor progression or occurrence of a likely health condition. As such, health care professionals, even if capable of reviewing the vast body of literature and data to determine appropriate likely health conditions based on demographics, would not be privy to corresponding information regarding wearable technology. Thus, providing a robust system and techniques for integrating information regarding wearable technology with medical information such as present in publications and medical databases represents a further technological improvement to the field of preventative and diagnostic medicine.

Health care services is a vitally important industry, and only becomes more so in light of the baby-boomer generation approaching the age range associated with many common diseases such as coronary heart disease, cancer, and various degenerative diseases. The drastic increase in the patient population associated with this transition will put great stress on the already-struggling industry. Health care professionals will need to improve the efficiency with which they can provide quality care to their growing body of patients, lest quality of care suffer due to the added strain. The presently disclosed inventive concepts facilitate improving quality of care by enabling health care professionals to leverage vast quantities of historical medical and demographic information in conjunction with information about wearable technology in order to predict likely health conditions based on patient demographics, as well as integrate these predictions with appropriate monitoring via wearable technology.

Thus, in various embodiments of the presently disclosed inventive concepts, the prediction of likely health conditions for a particular patient are based at least in part on relationships identified between different demographics attributes and associated health conditions, e.g. from a historical dataset; and the patient's personal health history.

In one general embodiment, a computer program product for determining likely health conditions based on demographic information includes a computer readable storage medium having program instructions embodied therewith, where the computer readable storage medium is not a transitory signal per se. The program instructions are executable by a processor to cause the processor to perform a method including: receiving historical demographic data comprising a plurality of attributes; associating the historical demographic data with one or more labels each independently corresponding to a known cause of a particular health condition; building a decision tree model based at least in part on the historical demographic data and the one or more labels associated therewith; generating, based on the decision tree model, a vector $Y_k$ representing one or more most probable causes of one or more of a plurality of health conditions; and determining one or more most likely health conditions for a patient based on comparing the vector $Y_k$ to a second vector $Z_k$, the second vector representing one or more most probable causes of one or more of the plurality of health conditions determined based on a health care record for the patient.

In accordance with another general embodiment, a computer program product for determining appropriate wearable technology and services to monitor a patient for a likely health condition includes a computer readable storage medium having program instructions embodied therewith, where the computer readable storage medium is not a transitory signal per se. The program instructions are executable by a processor to cause the processor to perform a method including: receiving textual data from one or more medical journals and one or more patient health records; identifying one or more concepts by applying one or more query rules to the textual data; generating an entity relationship graph based on the concepts; searching the entity relationship graph to determine one or more measurements associated with one or more most probable health conditions; and determining one or more wearable technologies associated with the one or more measurements.

In yet another general embodiment, a method for determining likely health conditions based on demographic information includes: receiving historical demographic data comprising a plurality of attributes; associating the historical demographic data with one or more labels each independently corresponding to a known cause of a particular health condition; building a decision tree model based at least in part on the historical demographic data and the one or more labels associated therewith; generating, based on the decision tree model, a vector $Y_k$ representing one or more most probable causes of one or more of a plurality of health conditions; and determining one or more most likely health conditions for a patient based on comparing the vector $Y_k$ to a second vector $Z_k$, the second vector representing one or more most probable causes of one or more of the plurality of health conditions determined based on a health care record for the patient.

FIG. 1 illustrates an architecture 100, in accordance with one embodiment. As shown in FIG. 1, a plurality of remote networks 102 are provided including a first remote network 104 and a second remote network 106. A gateway 101 may be coupled between the remote networks 102 and a proximate network 108. In the context of the present architecture 100, the networks 104, 106 may each take any form including, but not limited to a LAN, a WAN such as the Internet, public switched telephone network (PSTN), internal telephone network, etc.

In use, the gateway 101 serves as an entrance point from the remote networks 102 to the proximate network 108. As such, the gateway 101 may function as a router, which is capable of directing a given packet of data that arrives at the gateway 101, and a switch, which furnishes the actual path in and out of the gateway 101 for a given packet.

Further included is at least one data server 114 coupled to the proximate network 108, and which is accessible from the remote networks 102 via the gateway 101. It should be noted that the data server(s) 114 may include any type of computing device/groupware. Coupled to each data server 114 is a plurality of user devices 116. User devices 116 may also be connected directly through one of the networks 104, 106, 108. Such user devices 116 may include a desktop computer, lap-top computer, hand-held computer, printer or any other type of logic. It should be noted that a user device 111 may also be directly coupled to any of the networks, in one embodiment.

A peripheral 120 or series of peripherals 120, e.g., facsimile machines, printers, networked and/or local storage units or systems, etc., may be coupled to one or more of the networks 104, 106, 108. It should be noted that databases and/or additional components may be utilized with, or integrated into, any type of network element coupled to the networks 104, 106, 108. In the context of the present description, a network element may refer to any component of a network.

According to some approaches, methods and systems described herein may be implemented with and/or on virtual systems and/or systems which emulate one or more other systems, such as a UNIX system which emulates an IBM z/OS environment, a UNIX system which virtually hosts a MICROSOFT WINDOWS environment, a MICROSOFT WINDOWS system which emulates an IBM z/OS environment, etc. This virtualization and/or emulation may be enhanced through the use of VMWARE software, in some embodiments.

In more approaches, one or more networks 104, 106, 108, may represent a cluster of systems commonly referred to as a "cloud." In cloud computing, shared resources, such as processing power, peripherals, software, data, servers, etc., are provided to any system in the cloud in an on-demand relationship, thereby allowing access and distribution of services across many computing systems. Cloud computing typically involves an Internet connection between the systems operating in the cloud, but other techniques of connecting the systems may also be used.

Figure 2:
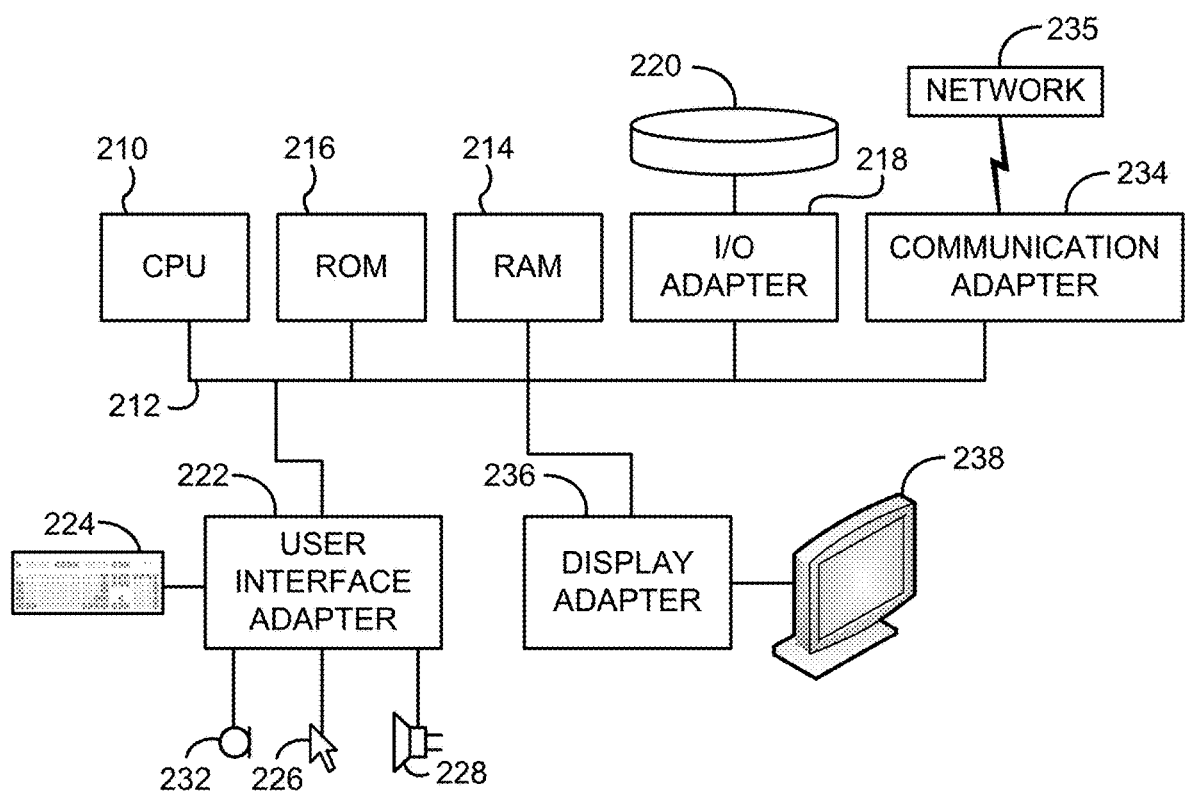
FIG. 2 shows a representative hardware environment that may be associated with the servers and/or clients of FIG. 1, in accordance with one embodiment.

FIG. 2 shows a representative hardware environment associated with a user device 116 and/or server 114 of FIG. 1, in accordance with one embodiment. Such figure illustrates a typical hardware configuration of a workstation having a central processing unit 210, such as a microprocessor, and a number of other units interconnected via a system bus 212.

The workstation shown in FIG. 2 includes a Random Access Memory (RAM) 214, Read Only Memory (ROM) 216, an I/O adapter 218 for connecting peripheral devices such as disk storage units 220 to the bus 212, a user interface adapter 222 for connecting a keyboard 224, a mouse 226, a speaker 228, a microphone 232, and/or other user interface devices such as a touch screen and a digital camera (not shown) to the bus 212, communication adapter 234 for connecting the workstation to a communication network 235 (e.g., a data processing network) and a display adapter 236 for connecting the bus 212 to a display device 238.

The workstation may have resident thereon an operating system such as the Microsoft Windows® Operating System (OS), a MAC OS, a UNIX OS, etc. It will be appreciated that a preferred embodiment may also be implemented on platforms and operating systems other than those mentioned. A preferred embodiment may be written using XML, C, and/or C++ language, or other programming languages, along with an object oriented programming methodology. Object oriented programming (OOP), which has become increasingly used to develop complex applications, may be used.

As discussed herein, logic may be implemented as a method on any device and/or system or as a computer program product, according to various embodiments.

Figure 3:
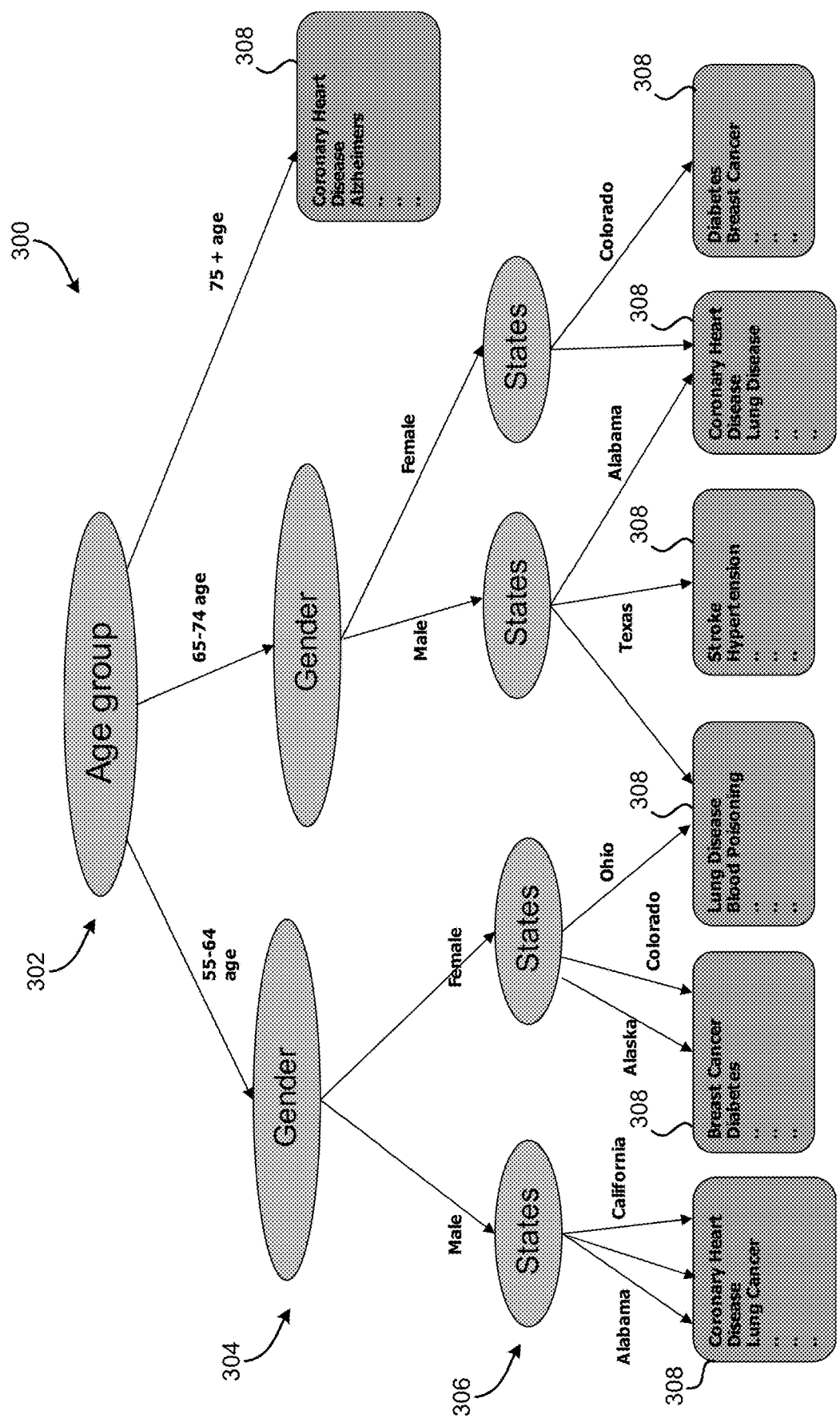
FIG. 3 illustrates a decision tree for modeling and predicting relevant health conditions based on demographics, in accordance with one embodiment.

Now referring to FIG. 3, a decision tree 300 for modeling and predicting relevant health conditions based on patient demographics is shown according to one embodiment. As shown in FIG. 3, the decision tree 300 includes three levels 302, 304, 306 each corresponding to a particular demographic attribute and a plurality of leaf nodes 308 each corresponding to one or more health conditions historically associated with patients satisfying a particular combination of demographic attributes. The internal nodes of the decision tree 300 each represent a division among possible values for a particular demographic attribute corresponding to the respective layer 302, 304, or 306 of the decision tree 300.

For example, in accordance with the embodiment shown in FIG. 3, layer 302 comprises a root node corresponding to the demographic attribute of "age" and represents a division according to one or more predetermined age groups that may be used to identify or eliminate relevant health conditions corresponding to each age group.

Layer 304, meanwhile, comprises two internal nodes and a leaf node 308 each corresponding to one of the age groups defined by the root node in layer 302. Those having ordinary skill in the art will appreciate that the decision tree 300 therefore need not be symmetric, and leaf nodes 308 may be present at various levels of a decision tree according to various embodiments of the presently disclosed inventive concepts.

According to the embodiment of FIG. 3, the internal nodes for layer 304 each correspond to the demographic attribute of "gender" (which, in the context of the present disclosures, may refer to biological characteristics, e.g. in the case of physical health conditions such as cancer, cardiovascular health conditions, reproductive health conditions, etc.; or identity characteristics, e.g. in the case of mental health conditions such as post-traumatic stress disorder, depression, etc.) and represent a division between the age groups reflected in layer 302 according to gender.

Meanwhile, the leaf node 308 of layer 304 corresponds to known, likely health conditions (Preferably, the known health conditions in the leaf nodes are the most likely K health conditions for a particular demographic or combination of demographics, where K is a predetermined number of health conditions determined relevant to report, e.g. based on the K health conditions corresponding to a predetermined threshold frequency, percentage, etc. of occurrence within the associated demographic, and/or based on a severity of the health condition(s)) to be experienced by members of the corresponding demographic. In one embodiment, K=5.

For instance, in the embodiment represented by FIG. 3, persons of a predetermined age or older (e.g. 75 years of age or more) may have a certain, high likelihood of experiencing one or more health conditions such as coronary heart disease, Alzheimer's disease, Parkinson's disease, etc. regardless of the person's gender, or place of residence. Accordingly, to maximize computational efficiency of providing relevant recommendations for personalized health care, the decision tree 300 may be built so as to predict the corresponding health conditions based on age alone. Of course, other dispositive demographics or demographic attributes may be employed with respect to different health conditions without departing from the scope of the presently disclosed inventive concepts. As referenced herein, demographic attributes should be understood to encompass a broad category within which various demographic groups may be defined, and demographics refer to the actual demographic group(s) to which various individuals may belong within a particular demographic attribute. For example, a demographic attribute of "age" may include demographics of 0-18, 19-29, 30-39, 40-54, 55-64, 65-74, and 75+.

For other health conditions which may be predicted with greater accuracy or certainty based on additional demographic information, the leaf nodes 308 may reside further down the tree. Accordingly, and with respect to the embodiment of FIG. 3, level 306 includes a plurality of internal nodes each corresponding to a demographic attribute of "current location of residence," and represent a plurality of different possible places where individuals may reside.

The possible places may be defined with any appropriate granularity that would be appreciated by persons having ordinary skill in the art of diagnostic and/or predictive medicine, and preferably are defined with a granularity that provides the greatest medical relevance to predicting health conditions for a particular patient population. For example, for an international patient population the particular places may include different countries, continents, regions (e.g. tropical, temperate, desert, mountain, jungle, island, etc.), while within a particular country the possible places may include different states, provinces, territories, etc., and while for a particular state the possible places may include different cities, municipalities, etc. As shown in FIG. 3, the internal nodes of level 306 reflect different states where an individual may reside within the United States of America.

With continuing reference to decision tree 300 as represented in FIG. 3, the leaf nodes 308 following level 306 represent the K most likely health conditions for patients satisfying the particular combination of age group, gender, and place of residence reflected by the progression from the root node in level 302 to the respective leaf node 308. For instance, according to leaf node 308 male patients aged 55-64 and living in Alabama, California, or Texas may be most likely to experience coronary heart disease and/or lung cancer, and these conditions may be predicted for patients within this demographic. As will be discussed in further detail below regarding method 500, a particularly advantageous aspect of the presently disclosed inventive concepts is to recommend personalized monitoring using appropriate wearable technology to monitor the progression or occurrence of the likely health conditions for the particular patient. This in turn allows earlier detection and treatment of such conditions, improving the duration and quality of life for the patient.

Preferably, the decision tree 300 is built so as to provide the best possible separation of possible health conditions as high in the tree (i.e. as close to the root node) as possible. As such, the root node preferably represents the demographic attribute that is most dispositive with respect to identifying a particular health condition. For example, different decision trees may be employed to determine most likely health conditions associated with different classes of diagnoses.

In one embodiment, a decision tree configured to determine likely health conditions associated with a particular type of disease known to only affect members of a particular demographic may employ as the root node the corresponding demographic attribute, thereby rapidly eliminating the possibility of patients not belonging to the particular demographic being predicted to experience the health condition(s) associated with the disease that only affects members of the particular demographic. In this manner, unnecessary treatments and/or medical procedures may be avoided, saving cost to the medical industry and the patient, as well as avoiding potential risks associated with such treatments and/or procedures.

In more embodiments, the decision tree 300 may include more or less levels, e.g. based on the number of demographic attributes relevant to predicting and modeling various health conditions, such as age bracket, gender, place of current residence, income level, place of birth, type of employment, lifestyle and/or environmental risk factors, ethnicity, etc. as would be understood by a person having ordinary skill in the art of diagnostic and/or predictive medicine.

Generally speaking, invoking the decision tree 300 as an algorithm may be represented according to the expression $(x, Y)=(x_1, x_2, x_3, x_4, \ldots x_n, Y)$, where $x_1$ to $x_n$ represent demographic values for n demographic attributes, and Y is a health condition associated with the particular combination of demographics represented by $x_1$ to $x_n$. Details of the algorithm will be discussed in further detail below regarding FIG. 4, according to one exemplary embodiment.

Figure 4:
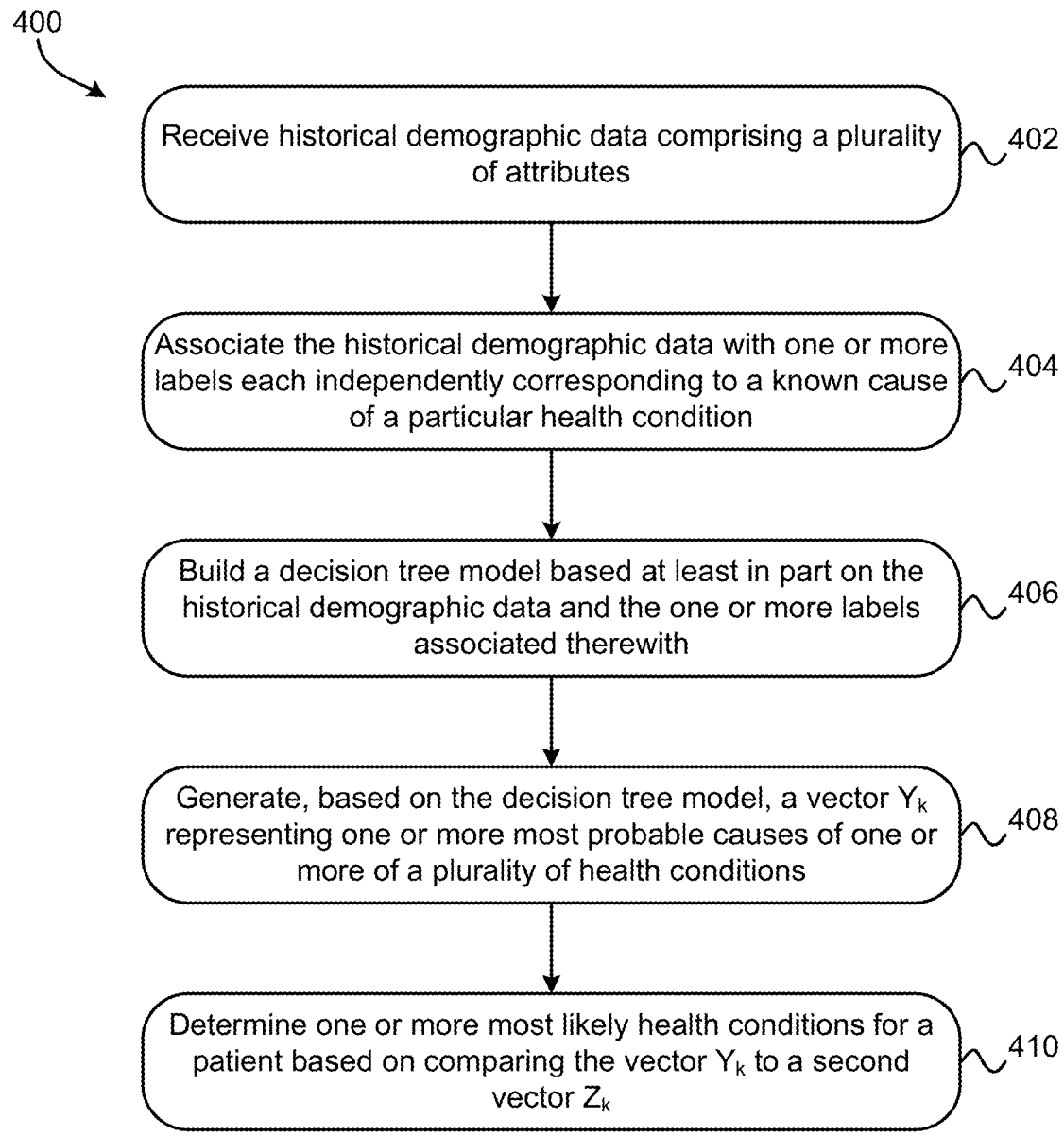
FIG. 4 illustrates a method for providing personalized health care based on demographics, in accordance with one embodiment.

Now referring to FIG. 4, a flowchart of a method 400 is shown according to one embodiment. The method 400 may be performed in accordance with the present invention in any of the environments depicted in FIGS. 1-3, among others, in various embodiments. Of course, more or less operations than those specifically described in FIG. 4 may be included in method 400, as would be understood by one of skill in the art upon reading the present descriptions.

Each of the steps of the method 400 may be performed by any suitable component of the operating environment. For example, in various embodiments, the method 400 may be partially or entirely performed by one or more servers, computers, or some other device having one or more processors therein. The processor, e.g., processing circuit(s), chip(s), and/or module(s) implemented in hardware and/or software, and preferably having at least one hardware component may be utilized in any device to perform one or more steps of the method 400. Illustrative processors include, but are not limited to, a central processing unit (CPU), an application specific integrated circuit (ASIC), a field programmable gate array (FPGA), etc., combinations thereof, or any other suitable computing device known in the art.

As shown in FIG. 4, method 400 includes operation 402, where historical demographic data comprising a plurality of attributes are received. For example, historical demographic data may include any combination of demographic attributes discussed herein, and is preferably associated with causes of health conditions experienced by the individuals represented within the historical demographic data. In preferred embodiments, the historical demographic data may be received in the form of a text string, which may be parsed from literature, publicly available medical databases, private medical databases, health care records, or any other suitable source of historical medical and/or demographic information and optionally formatted according to a desired convention using any suitable techniques that would be appreciated by persons having ordinary skill in the art of textual information parsing and formatting upon reading the present descriptions. In one embodiment world health organization (WHO) data may be the source of the historical medical and/or demographic information Furthermore, method 400 includes operation 404, in which the historical demographic data are associated with one or more labels each independently corresponding to a known cause of a particular health condition. In various approaches, each demographic value may be associated with a label, and/or combinations of demographic values may be associated with a label. Deciding the particular labels to apply to particular demographic(s) may be based in whole or in part on training a model using a decision tree algorithm $(x, Y)=(x_1, x_2, x_3, x_4, \ldots x_n, Y)$ as described herein with reference to FIG. 3.

In more embodiments, the labels may additionally or alternatively correspond, independently, to risk factors associated with particular health issues, such as environmental, behavioral, genetic, geographic, etc. risk factors including as exemplars such as consumption of particular substances (e.g. tobacco, alcohol, medications, etc.); lifestyle (e.g. active, sedentary, risk-seeking); travel history or planned travel (especially abroad); mutations or genetic expression information; etc. as would be appreciated by a person having ordinary skill in the art upon reading the instant disclosure.

Thus, and as shown in FIG. 4, method 400 involves building a decision tree model based at least in part on the historical demographic data and the one or more labels associated therewith in operation 406. The decision tree model may be constructed top-down (i.e. root to leaf) based on a training dataset D comprising the historical medical and/or demographic information. Moreover, the entropy and/or information gain may be computed for each attribute A, used for partitioning the decision tree at a given level of the tree. As understood herein, the entropy E may be defined as $E[D]=-\Sigma P(c_j) \log_2 P(c_j)$, while the information gain G may be defined as $G(D, A_i)=E[D]-E_{Ai}[D]$, and $P(c_j)$ is the probability of an element belonging to class $c_j$ in the dataset D.

Preferably, the Attribute A, that has the maximum Information Gain G for a given tree level is used to split the current tree, while minimizing the uncertainty to partition the dataset into different classes at that level. For example, and with reference to the exemplary embodiment of FIG. 3, the Attribute Value "Coronary Heart Disease" is the major cause of health issue in patients belonging to the demographic group of individuals age 75 or older. Hence, this attribute (age) has the maximum Information Gain for the Decision Tree branch of Age-Group 75 and above, and may be employed as the demographic attribute represented by the root node of the decision tree.

Additionally, as shown in FIG. 4, method 400 includes operation 408, in which a vector $Y_k$ representing one or more most probable causes of one or more of a plurality of health conditions is generated based at least in part on the decision tree model. The model, according to one illustrative approach, yields a vector $Y_k$ of causes of health issues or conditions $y_i$ and corresponding probabilities $p_i$, and takes the following form: $Y_k:(y_1:p_1, y_2:p_2, y_3:p_3, \ldots, y_n:p_n)$. This vector $Y_k$ may be sorted based on $p_i$ to compute the top-k causes of health issues or conditions. Subsequently, $Y_k$ may be provided for comparison to a second vector $Z_k$, as discussed further below with respect to operation 410.

In various approaches, building the decision tree model; generating the vector $Y_k$; and/or maximizing the information gain G while minimizing the entropy E may be based on a clustering of demographic values and/or attributes, the clustering being generated based on the historical medical and/or demographic information represented in dataset D. The clustering may be performed using any suitable technique that would be appreciated by a person having ordinary skill in the art upon reading these descriptions, without departing from the scope of the inventive concepts presented herein.

In operation 410, one or more most likely health conditions for a patient based on comparing the vector $Y_k$ to a second vector $Z_k$, where $Z_k$ represents one or more most probable causes of one or more of the plurality of health conditions determined based on a health care record for the patient. Similar to $Y_k$, the second vector $Z_k$ may take the following general form: $Z_k:(z_1:p_1, z_2:p_2, z_3:p_3, \ldots, z_n:p_n)$. Preferably, the comparison of $Y_k$ and $Z_k$ includes computing either a union, an intersection, or both, of $Y_k$ and $Z_k$. The union advantageously represents and predicts the top k health conditions that should be accounted for via appropriate treatment, monitoring, etc., while the intersection predicts a health plan with lesser coverage, but which may be more economically viable for the patient.

In particularly advantageous embodiments, the presently disclosed inventive techniques for identifying likely health conditions based on patient demographics may be coupled with techniques for identifying appropriate wearable technology in order to facilitate monitoring of a patient for occurrence of and/or progression toward the likely health conditions. This facilitates early detection and preventative action, by the health care professional and/or by the patient themselves, and therefore provides an improvement to the quality of care and quality of life experienced by the patient.

Figure 5:
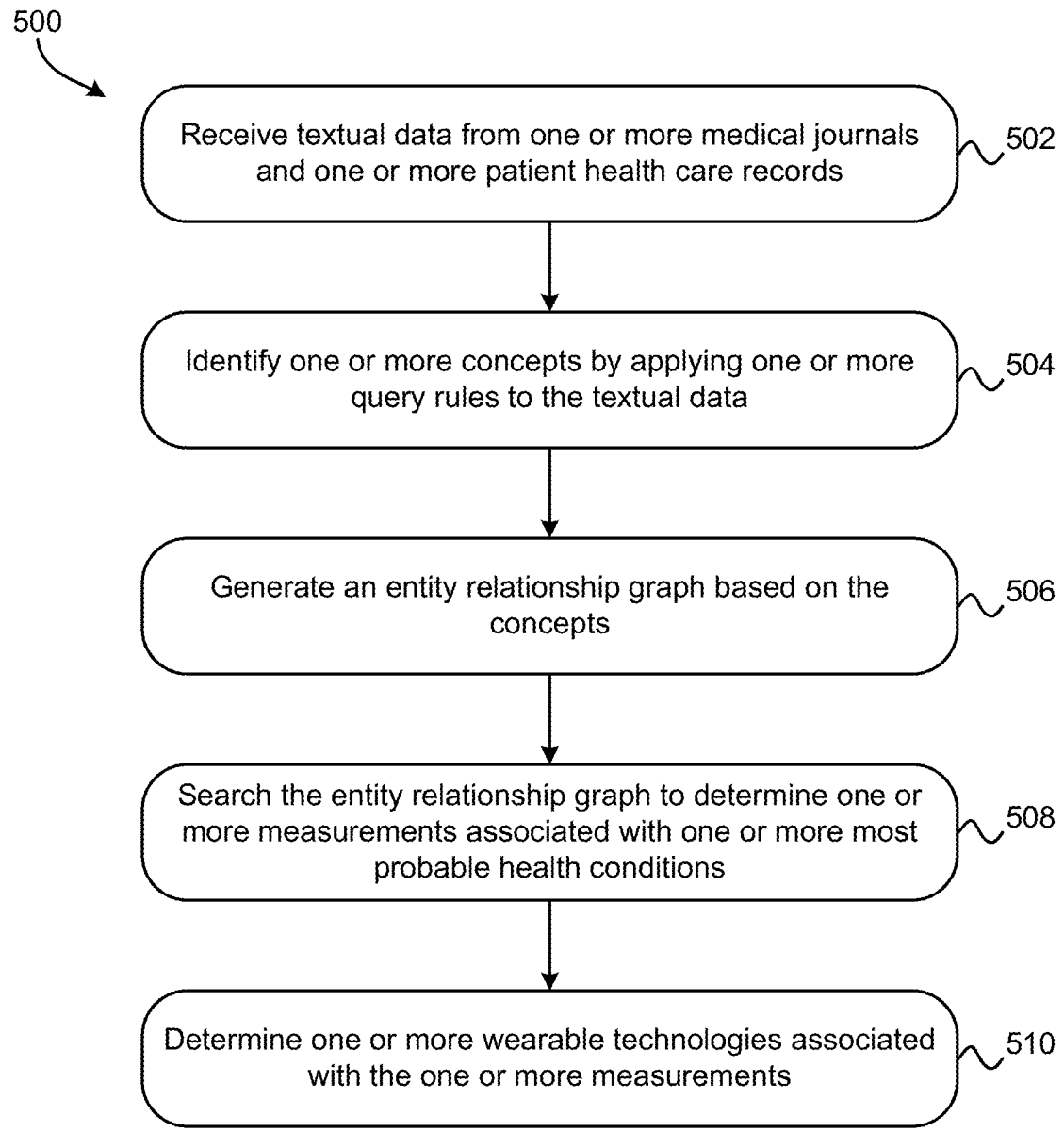
FIG. 5 illustrates a method for recommending appropriate wearables to monitor a health condition, in accordance with one embodiment.

In one approach, a suitable method 500 for identifying appropriate wearable technology to monitor a patient for a likely health condition is represented in FIG. 5 The method 500 may be performed in accordance with the present invention in any of the environments depicted in FIGS. 1-3, among others, in various embodiments. Of course, more or less operations than those specifically described in FIG. 5 may be included in method 500, as would be understood by one of skill in the art upon reading the present descriptions.

Each of the steps of the method 500 may be performed by any suitable component of the operating environment. For example, in various embodiments, the method 500 may be partially or entirely performed by one or more servers, computers, or some other device having one or more processors therein. The processor, e.g., processing circuit(s), chip(s), and/or module(s) implemented in hardware and/or software, and preferably having at least one hardware component may be utilized in any device to perform one or more steps of the method 500. Illustrative processors include, but are not limited to, a central processing unit (CPU), an application specific integrated circuit (ASIC), a field programmable gate array (FPGA), etc., combinations thereof, or any other suitable computing device known in the art.

As shown in FIG. 5, method 500 includes operation 502, where textual data are received, the textual data being from one or more medical journals, publications, databases, etc. and one or more patient health care records. The textual data may be received in any suitable form, but preferably are received in the form of a text string, which may be generated based on parsing available medical information such as noted above regarding FIG. 4 and operation 402.

Textual analytics may be applied to the received textual data, e.g. text analytics for identifying measurements (e.g. of bio-markers, vital statistics, etc.), to extract concepts from the textual data and identify relationships therebetween. For instance, in one embodiment of method 500, one or more concepts are identified in operation 504, by applying one or more query rules to the textual data.

The query rules may identify keywords that establish a causal relationship between different concepts, where the concepts each independently correspond to one or more topics selected from causes, health conditions, symptoms, measurements, and wearable technologies. Thus, in a preferred embodiment, the one or more query rules each independently represent a relationship selected from: a particular cause that corresponds to a particular disease or health condition, a particular symptom that corresponds to the particular disease or health condition, a particular measurement that corresponds to the particular symptom, and a particular wearable technology that corresponds to the particular measurement, e.g. a wearable technology configured to perform the particular measurement such as pulse rate, blood sugar or insulin level, breathing rate and/or volume, neurological activity, etc. as described herein and as would be understood by a person having ordinary skill in the art upon reading the present disclosure.

For example, in one embodiment textual data may indicate: (1) lung diseases are typically caused by smoking (linking a health condition to a cause); and (2) lung disease is exemplified by symptoms including prolonged cough, expectation of sputum, blood in sputum, fatigue, weakness, shortness of breath, and/or chest pain. Textual data may also indicate (3) that a normal respiration rate is in a range from approximately 12-20 breaths per minute, and (4) an existing wearable technology is available and is configured to track a user's physical activity, breathing rate, and state of mind. From this textual data, query rules may be developed establishing relationships between the cause and the health condition (per item 1); the symptoms associated with the health condition (per item 2); the appropriate measurements to monitor the patient for occurrence and/or progression of such symptoms (per item 3); and a suitable wearable device to recommend the patient use for monitoring purposes (per item 4).

Accordingly, in operation 506, method 500 involves generating an entity relationship graph based on the concepts extracted from the textual information. The entity graph may take any suitable form, and preferably includes an aggregation of relationships determined by extracting the concepts from the textual data. For instance, in one embodiment the relationships may be the edges of the graph, while extracted concepts are nodes of the graph.

With continuing reference to method 500 and FIG. 5, in operation 508 the entity relationship graph is searched to determine one or more measurements associated with one or more one or more most probable health conditions for the patient, e.g. based on identifying relationships between measurements and wearable technologies corresponding to the one or more most probable health conditions for the patient. The search may be performed using any suitable technique that would be appreciated by a person having ordinary skill in the art upon reading the present disclosures without departing from the scope of the inventive concepts presented herein.

Upon determining the measurements, one or more wearable technologies associated with the one or more measurements are determined in operation 510 of method 500, according to preferred embodiments.

The determination of wearable technology may include first determining whether any suitable wearable technology exists and is appropriate for the patient's use in monitoring their health status, and if so determining a most appropriate wearable (e.g. a wearable technology which is configured to measure the greatest number of measurements the patient should monitor) to recommend for the patient's use. A recommendation as to the patient's use of the appropriate wearable, and any appropriate services associated therewith (e.g. automated recording and reporting of data, alerts to the patient, etc.) may be rendered to the patient and/or health care professional, in some approaches.

If no appropriate wearable technology is available, the presently disclosed inventive concepts preferably include outputting an indication of such, and recommending the lack of such technology be reported, e.g. to an application or device developer who may then pursue a wearable technology to be implemented in the future and assist patients in monitoring their health status.

In various embodiments, the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Moreover, a system according to various embodiments may include a processor and logic integrated with and/or executable by the processor, the logic being configured to perform one or more of the process steps recited herein. By integrated with, what is meant is that the processor has logic embedded therewith as hardware logic, such as an application specific integrated circuit (ASIC), a FPGA, etc. By executable by the processor, what is meant is that the logic is hardware logic; software logic such as firmware, part of an operating system, part of an application program; etc., or some combination of hardware and software logic that is accessible by the processor and configured to cause the processor to perform some functionality upon execution by the processor. Software logic may be stored on local and/or remote memory of any memory type, as known in the art. Any processor known in the art may be used, such as a software processor module and/or a hardware processor such as an ASIC, a FPGA, a central processing unit (CPU), an integrated circuit (IC), a graphics processing unit (GPU), etc.

It will be clear that the various features of the foregoing systems and/or methodologies may be combined in any way, creating a plurality of combinations from the descriptions presented above.

It will be further appreciated that embodiments of the present invention may be provided in the form of a service deployed on behalf of a customer to offer service on demand.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A computer program product for determining likely health conditions based on demographic information, the computer program product comprising a tangible, non-transitory computer readable storage medium having program instructions embodied therewith, the program instructions executable by a processor to cause the processor to perform a method comprising:

receiving historical demographic data comprising a plurality of attributes;

associating the historical demographic data with one or more labels each independently corresponding to a known cause of a particular health condition;

building a decision tree model based at least in part on the historical demographic data and the one or more labels associated therewith, wherein building the decision tree model comprises:

computing an information gain G for the plurality of attributes;

computing an entropy E for the plurality of attributes;

wherein the entropy E for each given one of the plurality of attributes $A_i$ is defined as:

$$E[D] = -\Sigma P(c_j) \log_2 P(c_j);$$

wherein D is a training dataset comprising the historical demographic data;

wherein $P(c_j)$ is a probability of the given one of the plurality of attributes $A_i$ of the historical demographic data belonging to class $c_j$ in the dataset D; and wherein the information gain G for each of the given one of the plurality of attributes $A_i$ is defined as:

$$G(D, A_1) = E[D] - E_{Ai}[D];$$

and splitting the decision tree model according to one of the plurality of attributes having a maximum information gain for a given level of the decision tree model;

generating, based on the decision tree model, a vector $Y_k$ representing one or more most probable causes of one or more of a plurality of health conditions; and determining one or more most likely health conditions for a patient based on comparing the vector $Y_k$ to a second vector $Z_k$, the second vector representing one or more most probable causes of one or more of the plurality of health conditions determined based on a health care record for the patient;

wherein the vector $Y_k$ is a first two-dimensional array characterized by a first form:

$$Y_k: (y_1:p_1, y_2:p_2, y_3:p_3, \ldots, y_n:p_n);$$

wherein $y_1, y_2, y_3, \ldots y_n$ each independently represent one or more most probable causes of one of the plurality of health conditions;

wherein the $p_1, p_2, p_3, \ldots p_n$ of the first two-dimensional array each independently represent probabilities corresponding to the respective one or more most probable causes $y_1, y_2, y_3, \ldots y_n$ of the plurality of health conditions;

wherein the second vector $Z_k$ is a second two-dimensional array characterized by a second form:

$$Z_k: (z_1:p_1, z_2:p_2, z_3:p_3, \ldots, z_n:p_n);$$

wherein $z_1, z_2, z_3, \ldots z_n$ each independently represent one or more most probable causes of one a second plurality of health conditions, wherein the second plurality of health conditions are determined based on a health care record for the patient; and wherein the $p_1, p_2, p_3, \ldots p_n$ of the second two-dimensional array each independently represent probabilities corresponding to the respective one or more most probable causes of the second plurality of health conditions $z_1, z_2, z_3, \ldots z_n$.

2. The computer program product as recited in claim 1, wherein comparing $Y_k$ to $Z_k$ comprises computing a union of $Y_k$ and $Z_k$.

3. The computer program product as recited in claim 1, wherein comparing $Y_k$ to $Z_k$ comprises computing an intersection of $Y_k$ and $Z_k$.

4. The computer program product as recited in claim 1, wherein building the decision tree model and generating the vector $Y_k$ are further based on a clustering of the plurality of attributes.

5. The computer program product as recited in claim 1, wherein the plurality of attributes are selected from a group consisting of age bracket, current location of residence, place of birth, gender, income level, ethnicity, and employment type.

6. The computer program product as recited in claim 1, wherein the one or more labels include labels independently corresponding to one or more risk factors each independently corresponding to a known cause of a particular health condition.

7. The computer program product as recited in claim 1, further comprising program instructions executable by the processor to cause the processor to minimize uncertainty of one or more levels of the decision tree model by maximizing information gain G at the one or more levels.

8. The computer program product as recited in claim 1, comprising program instructions executable by the processor to cause the processor to:

determine one or more wearable technologies appropriate for monitoring the one or more of the plurality of health conditions;

monitor the one or more of the plurality of health conditions via the one or more wearable technologies; and alert the patient regarding the monitored one or more of the plurality of health conditions via the one or more wearable technologies.

9. A computer-implemented method for determining likely health conditions based on demographic information, the method comprising:

receiving, by the computer, historical demographic data comprising a plurality of attributes;

associating, by the computer, the historical demographic data with one or more labels each independently corresponding to a known cause of a particular health condition;

building, by the computer, a decision tree model based at least in part on the historical demographic data and the one or more labels associated therewith, wherein building the decision tree model comprises:

computing, by the computer, an information gain G for the plurality of attributes;

computing, by the computer, an entropy E for the plurality of attributes;

wherein the entropy E for each given one of the plurality of attributes $A_i$ is defined as:

$$E[D] = -\Sigma P(c_j) \log_2 P(c_j);$$

wherein D is a training dataset comprising the historical demographic data;

wherein $P(c_j)$ is a probability of the given one of the plurality of attributes $A_i$ of the historical demographic data belonging to class $c_j$ in the dataset D; and wherein the information gain G for each of the given one of the plurality of attributes $A_i$ is defined as:

$$G(D, A_i) = E[D] - E_{Ai}[D];$$

and splitting the decision tree model according to one of the plurality of attributes having a maximum information gain for a given level of the decision tree model;

generating, by the computer, based on the decision tree model, a vector $Y_k$ representing one or more most probable causes of one or more of a plurality of health conditions; and determining, by the computer, one or more most likely health conditions for a patient based on comparing the vector $Y_k$ to a second vector $Z_k$, the second vector representing one or more most probable causes of one or more of the plurality of health conditions determined based on a health care record for the patient;

wherein the vector $Y_k$ is a first two-dimensional array characterized by a first form:

$$Y_k : (y_1 : p_1, y_2 : p_2, y_3 : p_3, \ldots, y_n : p_n);$$

wherein $y_1, y_2, y_3, \ldots y_n$ each independently represent one or more most probable causes of one of the plurality of health conditions;

wherein the $p_1, p_2, p_3, \ldots p_n$ of the first two-dimensional array each independently represent probabilities corresponding to the respective one or more most probable causes $y_1, y_2, y_3, \ldots y_n$ of the plurality of health conditions;

wherein the second vector $Z_k$ is a second two-dimensional array characterized by a second form:

$$Z_k : (z_1 : p_1, z_2 : p_2, z_3 : p_3, \ldots, z_n : p_n);$$

wherein $z_1, z_2, z_3, \ldots z_n$ each independently represent one or more most probable causes of one a second plurality of health conditions, wherein the second plurality of health conditions are determined based on a health care record for the patient; and wherein the $p_1, p_2, p_3, \ldots p_n$ of the second two-dimensional array each independently represent probabilities corresponding to the respective one or more most probable causes of the second plurality of health conditions $z_1, z_2, z_3, \ldots z_n$.

10. The method as recited in claim 9, wherein comparing $Y_k$ to $Z_k$ comprises computing a union of $Y_k$ and $Z_k$.

11. The method as recited in claim 9, wherein comparing $Y_k$ to $Z_k$ comprises computing an intersection of $Y_k$ and $Z_k$.

12. The method as recited in claim 9, wherein building the decision tree model and generating the vector $Y_k$ are further based on a clustering of the plurality of attributes.

13. The method as recited in claim 9, wherein the plurality of attributes are selected from a group consisting of age bracket, current location of residence, place of birth, gender, income level, ethnicity, and employment type.

14. The method as recited in claim 9, wherein the one or more labels include labels independently corresponding to one or more risk factors each independently corresponding to a known cause of a particular health condition.

15. The method as recited in claim 9, further comprising minimizing an uncertainty of one or more levels of the decision tree model by maximizing the information gain at the one or more levels.

16. The computer program product as recited in claim 1, further comprising sorting the vector $Y_k$ to compute one or more top-k causes of the plurality of health conditions.

17. The computer program product as recited in claim 1, the method further comprising:

receiving textual data from one or more medical journals and one or more patient health records;

identifying one or more concepts by applying one or more query rules to the textual data, wherein the one or more query rules identify keywords that establish a causal relationship between the one or more concepts, wherein the causal relationship is selected from the group consisting of: the known cause that corresponds to the particular health condition, a symptom that corresponds to the particular health condition, a measurement that corresponds to the symptom, a wearable technology that corresponds to the measurement, and combinations thereof;

generating an entity relationship graph based on the concepts, wherein the entity graph comprises an aggregation of relationships determined by identifying the one or more concepts, wherein the relationships are edges of the entity graph, and wherein the one or more concepts are nodes of the entity graph;

searching the entity relationship graph to determine one or more measurements associated with one or more most probable health conditions;

determining one or more wearable technologies appropriate for monitoring the one or more of the plurality of health conditions;

recommending at least one of the one or more wearable technologies to be used for monitoring the one or more of the plurality of health conditions;

reporting a need for wearable technologies appropriate for monitoring the one or more of the plurality of health conditions to an application developer and/or a device developer;

monitoring the one or more of the plurality of health conditions via the one or more wearable technologies;

alerting the patient regarding the monitored one or more of the plurality of health conditions via the one or more wearable technologies;

minimizing an uncertainty of one or more levels of the decision tree model by maximizing the information gain G at the one or more levels of the decision tree model; and sorting the vector $Y_k$ to compute one or more top-k causes of the plurality of health conditions; and wherein building the decision tree model and generating the vector $Y_k$ are further based on a clustering of the plurality of attributes;

wherein the one or more labels include labels independently corresponding to one or more risk factors each independently corresponding to a known cause of a particular health condition;

wherein the plurality of attributes are selected from a group consisting of age bracket, current location of residence, place of birth, gender, income level, ethnicity, and employment type;

wherein building the decision tree model and generating the vector $Y_k$ are further based on a clustering of the plurality of attributes; and wherein comparing $Y_k$ to $Z_k$ comprises:
computing a union of $Y_k$ and $Z_k$, wherein the union represents and predicts a top k health conditions to be monitored; and
computing an intersection of $Y_k$ and $Z_k$, wherein the intersection predicts a health plan covering a subset of the top k health conditions to be monitored.

18. A computer program product for determining likely health conditions based on demographic information, the computer program product comprising a tangible, non-transitory computer readable storage medium having program instructions embodied therewith, wherein the computer readable storage medium is not a transitory signal per se, the program instructions executable by a processor to cause the processor to perform a method comprising:

receiving historical demographic data comprising a plurality of attributes;

computing an entropy E for the plurality of attributes, wherein the entropy E for each given one of the plurality of attributes $A_i$ is defined as:

$$E[D] = -\Sigma P(c_j) \log_2 P(c_j);$$

wherein D is a training dataset comprising the historical demographic data;

wherein $P(c_j)$ is a probability of the given one of the plurality of attributes $A_i$ of the historical demographic data belonging to class $c_j$ in the dataset D;

associating the historical demographic data with one or more labels each independently corresponding to a known cause of a particular health condition; and building a decision tree model based at least in part on the historical demographic data and the one or more labels associated therewith, wherein building the decision tree model comprises:

computing an information gain G for the plurality of attributes, wherein the information gain G for each of the given one of the plurality of attributes $A_i$ in dataset D is defined as:

$$G(D, A_i) = E[D] - E_{Ai}[D];$$

and splitting the decision tree model according to one of the plurality of attributes having a maximum information gain for a given level of the decision tree model;

generating, based on the decision tree model, a vector $Y_k$ representing one or more most probable causes of one or more of a plurality of health conditions; and determining one or more most likely health conditions for a patient based on comparing the vector $Y_k$ to a second vector $Z_k$, the second vector representing one or more most probable causes of one or more of the plurality of health conditions determined based on a health care record for the patient.

19. The method as recited in claim 9, further comprising:

receiving textual data from one or more medical journals and one or more patient health records;

identifying one or more concepts by applying one or more query rules to the textual data, wherein the one or more query rules identify keywords that establish a causal relationship between the one or more concepts, wherein the causal relationship is selected from the group consisting of: the known cause that corresponds to the particular health condition, a symptom that corresponds to the particular health condition, a measurement that corresponds to the symptom, a wearable technology that corresponds to the measurement, and combinations thereof;

generating an entity relationship graph based on the concepts, wherein the entity graph comprises an aggregation of relationships determined by identifying the one or more concepts, wherein the relationships are edges of the entity graph, and wherein the one or more concepts are nodes of the entity graph;

searching the entity relationship graph to determine one or more measurements associated with one or more most probable health conditions;

determining one or more wearable technologies appropriate for monitoring the one or more of the plurality of health conditions;

recommending at least one of the one or more wearable technologies to be used for monitoring the one or more of the plurality of health conditions;

reporting a need for wearable technologies appropriate for monitoring the one or more of the plurality of health conditions to an application developer and/or a device developer;

monitoring the one or more of the plurality of health conditions via the one or more wearable technologies;

alerting the patient regarding the monitored one or more of the plurality of health conditions via the one or more wearable technologies;

minimizing an uncertainty of one or more levels of the decision tree model by maximizing the information gain G at the one or more levels of the decision tree model; and sorting the vector $Y_k$ to compute one or more top-k causes of the plurality of health conditions; and wherein building the decision tree model and generating the vector $Y_k$ are further based on a clustering of the plurality of attributes;

wherein the one or more labels include labels independently corresponding to one or more risk factors each independently corresponding to a known cause of a particular health condition;

wherein the plurality of attributes are selected from a group consisting of age bracket, current location of residence, place of birth, gender, income level, ethnicity, and employment type;

wherein building the decision tree model and generating the vector $Y_k$ are further based on a clustering of the plurality of attributes; and wherein comparing $Y_k$ to $Z_k$ comprises:
  computing a union of $Y_k$ and $Z_k$, wherein the union represents and predicts a top k health conditions to be monitored; and
  computing an intersection of $Y_k$ and $Z_k$, wherein the intersection predicts a health plan covering a subset of the top k health conditions to be monitored.

* * * * *